United States Patent
Brown

(10) Patent No.: US 10,757,226 B2
(45) Date of Patent: *Aug. 25, 2020

(54) AUTOMATED DELIVERY OF MEDICAL DEVICE SUPPORT SOFTWARE

(71) Applicant: ZOLL Medical Corporation, Chelmsford, MA (US)

(72) Inventor: Eric W. Brown, Saugus, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/256,927

(22) Filed: Jan. 24, 2019

(65) Prior Publication Data

US 2019/0230193 A1 Jul. 25, 2019

Related U.S. Application Data

(63) Continuation of application No. 15/354,156, filed on Nov. 17, 2016, now Pat. No. 10,230,823, which is a continuation of application No. 13/652,285, filed on Oct. 15, 2012, now Pat. No. 9,531,837.

(60) Provisional application No. 61/592,386, filed on Jan. 30, 2012, provisional application No. 61/547,570, filed on Oct. 14, 2011.

(51) Int. Cl.
*H04L 29/06* (2006.01)
*H04L 29/08* (2006.01)
*A61N 1/39* (2006.01)
*A61M 1/10* (2006.01)

(52) U.S. Cl.
CPC .............. *H04L 67/42* (2013.01); *A61M 1/10* (2013.01); *A61N 1/3925* (2013.01); *A61N 1/3993* (2013.01); *H04L 67/12* (2013.01); *H04L 67/141* (2013.01); *H04L 67/34* (2013.01); *A61M 2205/3584* (2013.01); *H04L 67/02* (2013.01)

(58) Field of Classification Search
CPC .............................. H04L 67/42; A61N 1/3925
See application file for complete search history.

(56) References Cited

U.S. PATENT DOCUMENTS

| 9,531,837 B2 | 12/2016 | Brown |
| 10,230,823 B2 | 3/2019 | Brown |
| 2004/0202132 A1 | 10/2004 | Heinonen et al. |
| 2004/0204743 A1 | 10/2004 | McGrath et al. |
| 2005/0216311 A1 | 9/2005 | Gmelin et al. |
| 2006/0031378 A1 | 2/2006 | Vallapureddy et al. |
| 2007/0027506 A1 | 2/2007 | Stender et al. |
| 2007/0080223 A1 | 4/2007 | Japuntich |

(Continued)

FOREIGN PATENT DOCUMENTS

WO   WO-2006108304 A1   10/2006

OTHER PUBLICATIONS

Extended European Supplementary Search Report issued in EP 12840431.6 dated Feb. 10, 2015 (8 pages).

(Continued)

*Primary Examiner* — Michael A Keller
*Assistant Examiner* — Jsing Forng Lin
(74) *Attorney, Agent, or Firm* — Finch & Maloney PLLC

(57) ABSTRACT

Embodiments of the present invention include a portable medical device with an integrated web server. The portable medical device is configured to establish a communication session with a user device. The integrated web server is configured to load software onto the user computing device for exchanging data with the portable medical device.

19 Claims, 4 Drawing Sheets

(56) References Cited

U.S. PATENT DOCUMENTS

| | | | |
|---|---|---|---|
| 2008/0091175 A1 | 4/2008 | Frikart et al. |
| 2008/0249590 A1 | 10/2008 | Simms |
| 2009/0099864 A1 | 4/2009 | Cronrath et al. |
| 2009/0204422 A1 | 8/2009 | James et al. |
| 2009/0276515 A1 | 11/2009 | Thomas et al. |
| 2010/0049010 A1 | 2/2010 | Goldreich |
| 2010/0292556 A1 | 11/2010 | Golden |
| 2011/0060378 A1 | 3/2011 | Tuysserkani |
| 2011/0115624 A1 | 5/2011 | Tran |
| 2011/0219090 A1 | 9/2011 | Chan et al. |
| 2012/0072895 A1 | 3/2012 | Koyama et al. |
| 2012/0136404 A1 | 5/2012 | Drew et al. |
| 2012/0296384 A1 | 11/2012 | Daynes et al. |
| 2013/0013339 A1 | 1/2013 | Goldman et al. |
| 2013/0145141 A1 | 6/2013 | Han et al. |
| 2013/0211265 A1 | 8/2013 | Bedingham et al. |
| 2017/0272316 A1 | 9/2017 | Johnson et al. |

OTHER PUBLICATIONS

International Search Report and Written Opinion issued in PCT/US2012/060254 dated Dec. 27, 2012, (15 pages).

European Supplementary Search Report issued in EP12840431.6, dated Feb. 10, 2015, 8 pages.

US 10,757,226 B2

AUTOMATED DELIVERY OF MEDICAL DEVICE SUPPORT SOFTWARE

CROSS-REFERENCE TO RELATED APPLICATIONS

This application is a Continuation of prior application Ser. No. 15/354,156, filed on Nov. 17, 2016 (now U.S. Pat. No. 10,230,823), which is itself a Continuation of prior application Ser. No. 13/652,285, filed on Oct. 15, 2012 (now U.S. Pat. No. 9,531,837), which claims the benefit of U.S. Provisional Patent Application Ser. No. 61/547,570, filed on Oct. 14, 2011, and U.S. Provisional Patent Application Ser. No. 61/592,386, filed on Jan. 30, 2012, all of which are incorporated by reference herein in their entireties for all purposes.

TECHNICAL FIELD

Embodiments of the present invention relate generally to emergency medical devices, and more specifically to applications for communicating with such devices.

BACKGROUND

Existing devices for use in emergency medical response situations, for example defibrillators, often each have their own software applications providing an interface for receiving data from such devices. For example, a defibrillator device may include a physical interface (such as a serial port or Ethernet interface) for connecting the defibrillator with a personal computer. The user must install device application software onto the personal computer, either by download or using physical media provided to the user, for example a DVD-ROM with the device software. This application software enables the exchange of data and, in some cases, control of the medical device by the computing device.

However, distributing device application software in this way requires that the software developer provide separate development efforts based on target hardware and software platforms, for example MS-Windows, Mac OS X, Linux, iOS, Android, and Windows Mobile. Maintenance and upgrades for such software can also be challenging, as it requires redistribution of software and must often be carefully synchronized with vendor-specific upgrades. The makers of such software and devices also often have difficulty tracking which user is using which version of software; furthermore, the fact that a particular version of software was delivered to a user does not always mean that the user installed that particular version.

SUMMARY

In Example 1, a portable medical device according to an embodiment of the present invention includes a communication system, a web application server configured to create a server-client communications connection with a user device via the communication system, wherein the web application server is further configured to automatically send to the user device a software application to be run on the user device which will permit the user device to access data from the portable medical device, and may also permit the user device to exchange information and data with the medical device, for example configuration information, patient data, and/or initiation of internal checks.

In Example 2, the portable medical device of Example 1, wherein the portable medical device is a defibrillator.

In Example 3, the portable medical device of Example 1, wherein the portable medical device is an AED.

In Example 4, the portable medical device of Example 1, wherein the portable medical device is a non-invasive cardiac support pump.

In Example 5, the portable medical device of Example 1, wherein the portable medical device is a wearable cardioverter defibrillator.

In Example 6, the portable medical device of any of Examples 1-4, wherein the web application server is further configured to prompt automatic reboot of the user device upon the user device's receipt of the software application.

In Example 7, the portable medical device of any of Examples 1-6, wherein the web application server is further configured to prompt automatic display on the user device of a prompt asking for confirmation of the installation of the software application, for example upon reboot.

In Example 8, a method for automated delivery of application software supporting the hardware/software capabilities of a medical device according to embodiments of the present invention includes establishing a server-client communications connection with a user device with a web application server embedded in a medical device, automatically sending to the user device a software application to be run within a web browser of the user device, and sending data from the medical device to the software application running in the web browser.

In Example 9, the method of Example 8, wherein the medical device is a defibrillator and the user device is a computing device.

In Example 10, the method of Example 8, wherein the medical device is an AED.

In Example 11, the method of Example 8, wherein the medical device is a noninvasive cardiac support pump.

In Example 12, the method of Example 8, wherein the medical device is a wearable cardioverter defibrillator.

In Example 13, the method of any of Examples 8-12, further comprising prompting automatic reboot of the user device upon the user device's receipt of the software application.

In Example 14, the method of any of Examples 8-13 further comprising initiating automatic display on the user device of a prompt asking for confirmation of the installation of the software application upon reboot.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
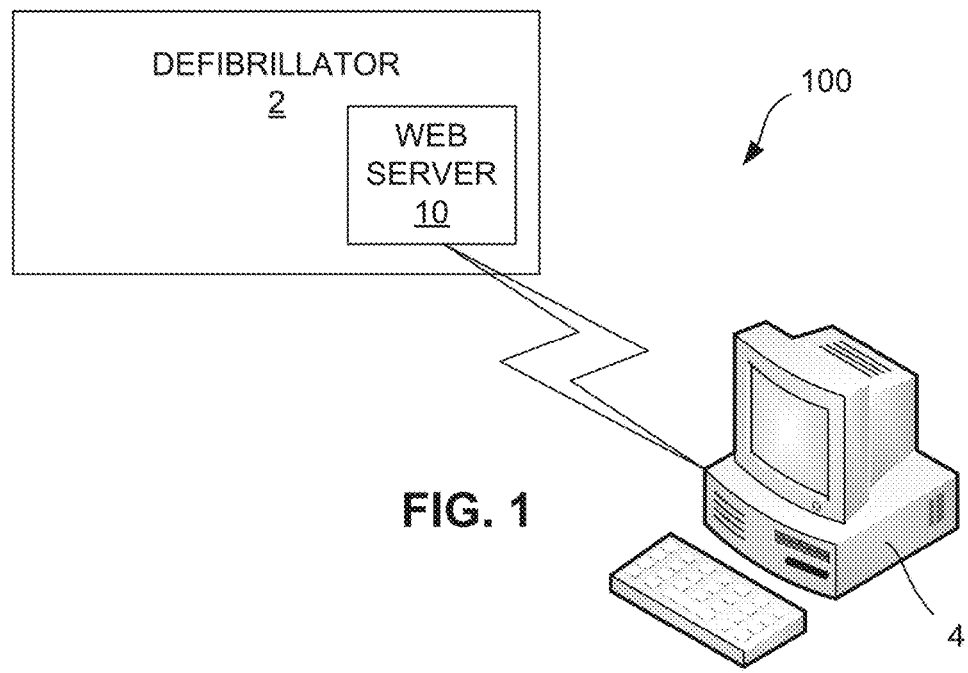
FIG. 1 illustrates a conceptual diagram of a medical device with a web server capable of serving applications to a client device, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 3:
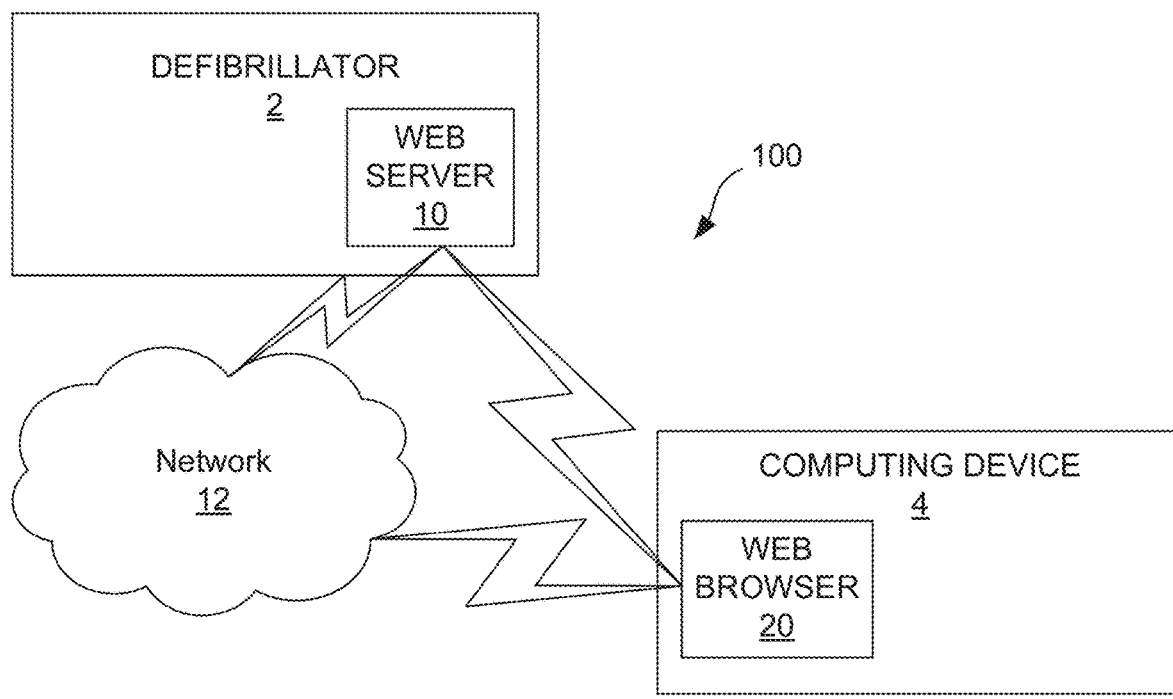
FIG. 3 illustrates the system of FIG. 1 with a web browser 20 in the client device, according to embodiments of the present invention.

FIGS. 1 and 3 illustrate a system 100 for communication between a device 2 and a user device 4, according to embodiments of the present invention. As used herein, the term "user device" is used in its broadest sense to refer to any computing device, and may also be referred to as a user computing device, a client device, a computer system, a client computing device, and a client computing user device. The device 2 may be a medical device, for example a defibrillator, automatic external defibrillator (AED), a non-invasive cardiac support pump (for example a ZOLL® AutoPulse® device), a wearable cardioverter defibrillator (for example a ZOLL® LifeVest® device), and the like. User device 4 may be a personal computer or other computing device capable of running web applications, for example a mobile phone, an iPad®, and/or a personal computer. User device 4 may also be a medical device, for example the same kind of device as device 2, according to embodiments of the present invention. Device 2 may include a web server 10, according to embodiments of the present invention, and device 4 may include a web browser 20 configured to interact with the web server 10 of device, for example using Internet Protocol and/or Hypertext Transfer Protocol and/or other similar protocols, according to embodiments of the present invention. Although element 20 is described as a browser, element 20 may also be a web client, which may or may not include a user interface component, and which may use web protocols for the interaction with the web server, according to embodiments of the present invention. Web interactions need not be limited to the exchange of web pages; web service protocols including REST, XML-RPC, JSON-RPC, SOAP, and PB may also be used. Embodiments of the present invention work with wired and/or wireless and/or other communications connections which support a web server delivering content.

Embodiments of the present invention provide an ability to better manage device-specific or operating system-specific software applications by embedding a web application server 10 into the device 2 hardware. For device software code that is designed to work cross-platform, the web server 10 is configured to automatically serve a version of the software to the user's computer 4 which matches the version of the device 2 installed onto the user's computer, according to embodiments of the present invention. In other words, in order to interoperate with client computing devices 4 that are cross platform, the web server 10 is configured to automatically serve the appropriate supporting application software to the target client computing device 4 that supports the functional capabilities of the medical device 2, according to embodiments of the present invention. The software application will automatically get upgraded (or downgraded) as necessary based upon what is done to the baseline software of the device 2, and multiple versions of the application will get transparently used as necessary (by client machine 4) for users using multiple versions of the same device 2, according to embodiments of the present invention As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network or a series of devices and/or communication protocols, or direct coupling. For example, "communicably coupled" may include coupled wirelessly via Wi-Fi and/or BlueTooth®. The device 2 and device 4 may also be coupled via an ad hoc, self-configuring, self-healing network, according to embodiments of the present invention.

Embodiments of the present invention include a device 2 with a web server 10 embedded therein, in addition to the conventional code for running the device 2. The web server 10 may be configured to target the web browser 20 of the device 4 as a sort of platform within a platform, which permits the manufacturer of device 2 to design for a much larger hardware and operating system cross section. The manufacturer of device 2 may also benefit as third parties upgrade the performance of their products, according to embodiments of the present invention. According to some embodiments of the present invention, the software for device 2 and web server 10 may launch larger and more powerful applications for management within external device's 4 caching space by external devices 4 themselves, which may provide transparent version control for the device 2 manufacturer and a more seamless customer experience across devices 2.

According to some embodiments of the present invention, the applications served by device 2 and server 10 are treated as blocks of data by the devices 2 themselves. Although such applications reside within device 2 in order to be served by them, the device 2 does not execute the application code, and instead all code execution occurs on the client-side machines 4, according to embodiments of the present invention. As such, the device 2 and server 10 may act simply as a delivery agent for the software, according to embodiments of the present invention.

Figure 4:
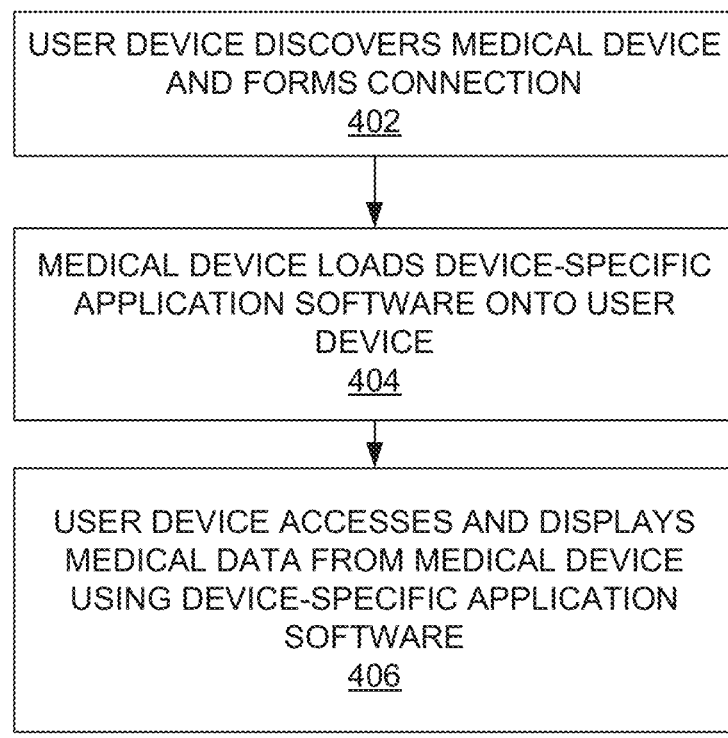
FIG. 4 depicts a flow chart illustrating a device web server connection method, according to embodiments of the present invention.

Embodiments of the present invention employ standard auto-discovery systems like Bonjour, Zeroconf, mDNS, Avahi, and the like to set up ad hoc connections between device 2 and client computer 4 without requiring any additional hardware or supporting network. Device 2 has computing power to run a web server 10, auto-advertising protocols, and to serve any required combination of JavaScript, HTML, CSS, RDF, JSON, SVG, XML, RSS, and the like kinds of files, according to embodiments of the present invention. As illustrated in FIG. 4, a user device 4 discovers a medical device 2 and forms a wireless connection (block 402). The medical device 2 loads device-specific (and target client computing device platform-appropriate) application software onto the user device 4 (block 404). The user device 4 accesses and displays medical data from medical device 2 using the device-specific application software (block 406), according to embodiments of the present invention. According to some embodiments of the present invention, the user device 4 has an ability to edit information or data on the medical device 2, for example to display and edit the configuration information, or patient demographic information. User device 4 may also initiate some device 2 internal services, for example running diagnostics and/or having diagnostic results returned to device 4, according to embodiments of the present invention. The device 2 and/or server 10 has the capability to auto-advertise its presence, for example with an active wireless signal. The device 4 may find device 2 and/or server 10 using one or more auto-discovery protocols, according to embodiments of the present invention.

Although FIGS. 1 and 3 illustrate a direct wireless connection between devices 2 and 4, the devices 2 and 4 may also be connected via a network, for example via the Internet, according to embodiments of the present invention. The device 2 may be configured to arbitrarily code data into an arbitrary number of formats, and make the data available to any web browser 20 on any device, according to embodiments of the present invention. According to some embodiments of the present invention, the device 2 may include a global positioning system (GPS), and may be configured to provide client web browsers 20 with reports on its location, its identity, remote location, and remote diagnostics.

According to some embodiments of the present invention, as described above, the device 4 discovers and connects with the device 2 automatically, and the web server automatically loads the device-specific application software onto device 4. Device 4 may then automatically reboot, and/or the next time device 4 is rebooted, may prompt the user on device startup to confirm the installation of the software provided by web server 10, according to embodiments of the present invention. If such program installation failed, then the device 4 may be configured to send an error report or fault report back to the device 2 manufacturer, either via device 2 or via another internet connection, according to embodiments of the present invention. The web server 10 could also be used to enable other peripheral devices, for example configuring a Bluetooth® keyboard to work to enter data into device 2. As another example, instead of installing a microphone in device 2, the server 10 could simply load software onto a Bluetooth® audio device to configure it to provide audio information to device 2. For example, such an audio device may be a headset which is configured to provide audio input and/or output. For example, if device 2 is a defibrillator or a cardiopulmonary resuscitation (CPR) assisting device, audio or voice prompts for CPR could be provided from device 2 into such a headset, according to embodiments of the present invention.

Figure 2:
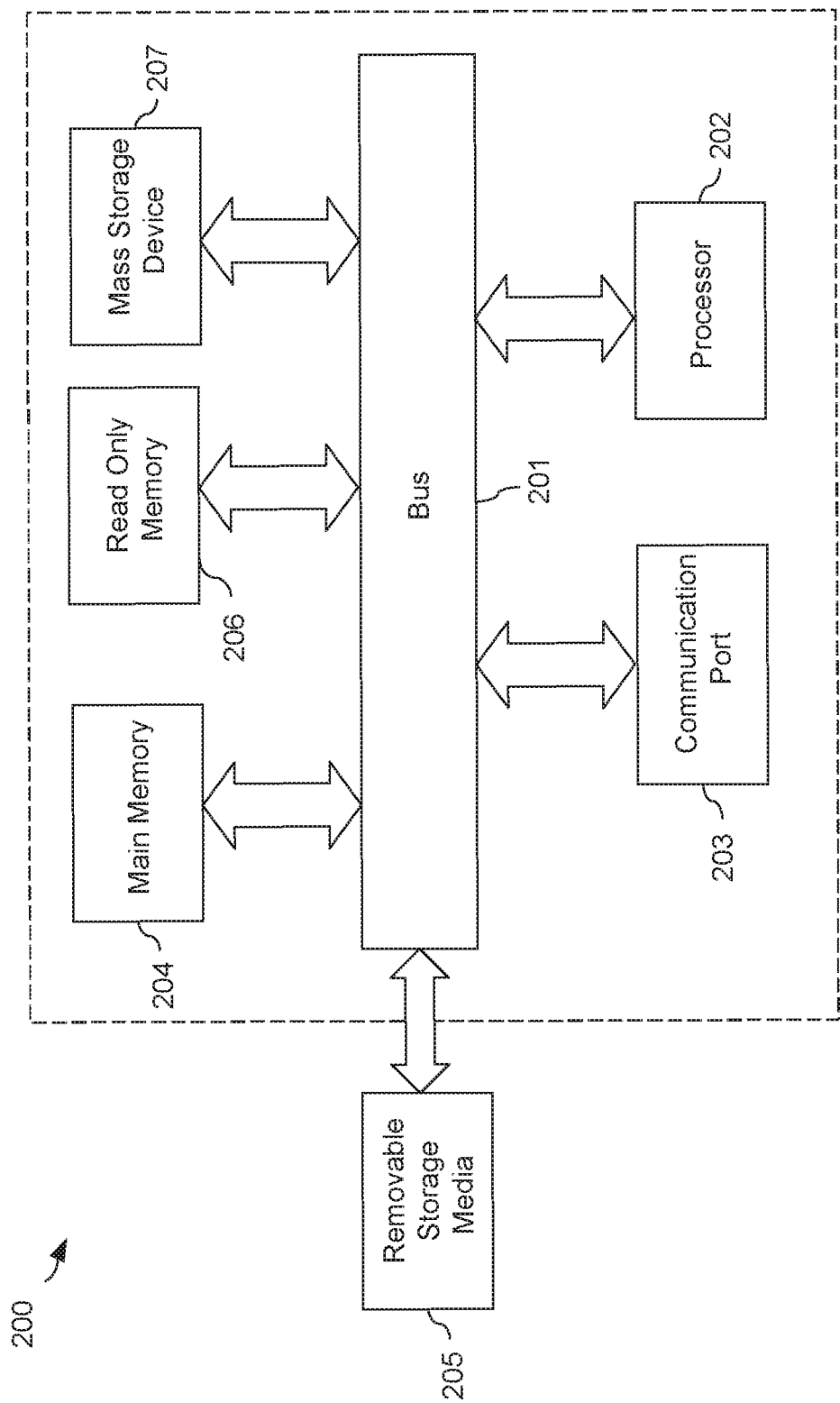
FIG. 2 illustrates a computer system, or computing device system, according to embodiments of the present invention.

FIG. 2 is an example of a computer or computing device system 200 with which embodiments of the present invention may be utilized. For example, defibrillator 2 and/or computing device 4 may be or incorporate a computer system 200, according to embodiments of the present invention. According to the present example, the computer system includes a bus 201, at least one processor 202, at least one communication port 203, a main memory 204, a removable storage media 205, a read only memory 206, and a mass storage 207.

Processor(s) 202 can be any known processor, such as, but not limited to, an Intel® Itanium® or Itanium 2® processor(s), or AMD® Opteron® or Athlon MP® processor(s), or Motorola® lines of processors, or any known microprocessor or processor for a mobile device, such as, but not limited to, ARM, Intel Pentium Mobile, Intel Core i5 Mobile, AMD A6 Series, AMD Phenom II Quad Core Mobile, or like devices. Communication port(s) 203 can be any of an RS-232 port for use with a modem based dialup connection, a copper or fiber 10/100/1000 Ethernet port, or a Bluetooth® or WiFi interface, for example. Communication port(s) 203 may be chosen depending on a network such a Local Area Network (LAN), Wide Area Network (WAN), or any network to which the computer system 200 connects. Main memory 204 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, flash memory or other storage media may be used, including removable or dedicated memory in a mobile or portable device, according to embodiments of the present invention. As another example, hard disks such as the Adaptec® family of SCSI drives, an optical disc, an array of disks such as RAID (e.g. the Adaptec family of RAID drives), or any other mass storage devices may be used. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, zip drives, compact disc—read only memory (CD-ROM), compact disc—re-writable (CD-RW), or digital video disk—read only memory (DVD-ROM), for example. The components described above are meant to exemplify some types of possibilities. In no way should the aforementioned examples limit the scope of the invention, as they are only exemplary embodiments of computer system 400 and related components.

As illustrated in FIG. 3, server 10 may be configured to not only provide content (e.g. software applications or medical data from device 2), but it may also be configured to provide one or more links to web browser 20, thereby providing web browser 20 with information for finding and accessing such information on another device on a network 12. The web browser 20 may be configured to access such content via the link through its own connection to the network 12, such as the Internet, if it has such a connection, and/or may be configured to access such content via the link through a network 12 connection of the web server 10, according to embodiments of the present invention. Web server 10 may provide such links for content which may be dynamic or changing over time, for example.

Figure 5:
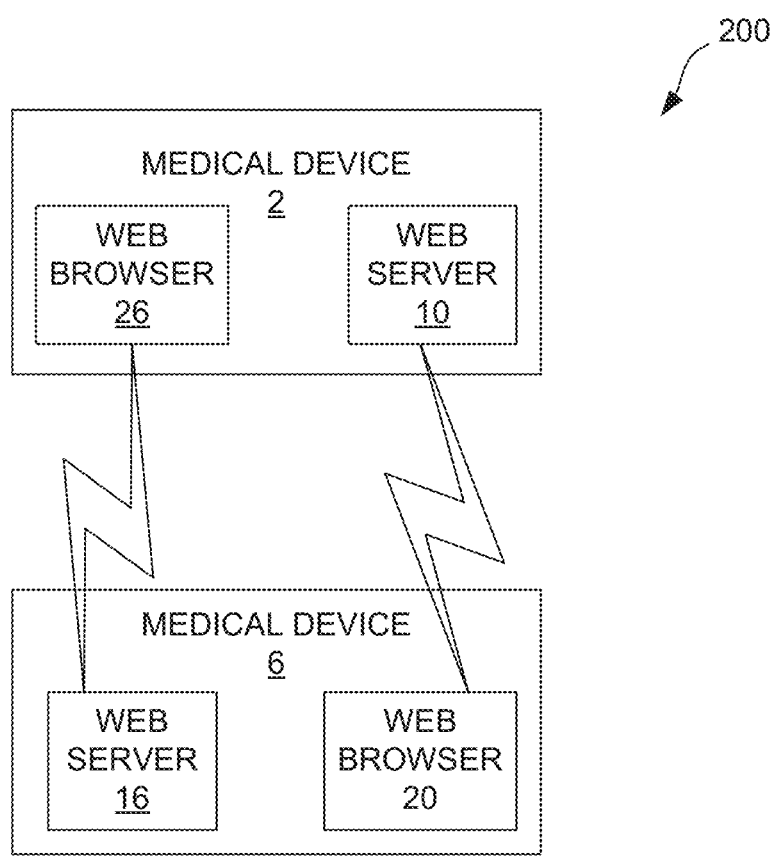
FIG. 5 illustrates a system with two medical devices connected, each having a web server and a web client, according to embodiments of the present invention.

As shown in FIG. 5, system 200 may be configured to permit web server 10 to communicate not only with a computing device, but with a computing device that is another medical device 6, such as, for example, another defibrillator or another type of medical device, according to embodiments of the present invention. Medical device 6 may include a web server 16 and/or web client 20, according to embodiments of the present invention. The medical device 6 may be configured to auto-discover another medical device 2, permit an automatic server-client communication to be established between server 10 and client 20, and may even be configured to permit device 2 to automatically take control of one or more functions of device 6 (e.g. according to a "master-slave" relationship), according to embodiments of the present invention. Browser 26 may, in the same or a similar fashion, be configured to automatically connect with server 16, for example using an auto-discovery protocol, according to embodiments of the present invention. Devices 2, 6 configured in this way may also permit viral distribution of software and/or other content. For example, once device 2 has connected to device 6 and installed or otherwise implemented the software on device 6 for communicating with device 2, another web browser enabled device (not shown) which is not within the range of device 2, or is not otherwise in communication with device 2, may instead automatically connect with the web server 16 of device 6 and receive the same type of software and/or content. This permits software, content, and/or updates thereto to be distributed across multiple devices in a viral fashion, according to embodiments of the present invention.

According to some embodiments of the present invention, the web server need not be restricted to typical embedded languages like C or C++. Modern interpreted and just-in-time compiled languages like Python and JavaScript can also be used for server implementation. Event-driven approaches found in these languages (like Twisted for Python and promises for JavaScript) offer many advantages that make them potentially better design choices than the more traditional offerings, according to embodiments of the present invention. JavaScript in particular makes it possible to directly share code between server and client, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical device communications system, comprising:
a communication network;
a first defibrillator comprising at least one first processor and memory, the first defibrillator configured to be enabled as a web server in a server-client communications connection; and
a second defibrillator comprising at least one second processor and memory, the second defibrillator configured to be enabled as a web client in the server-client communications connection and further configured to:
establish the server-client communications connection with the web server of the first defibrillator via the communication network to permit data exchange between the first defibrillator and the second defibrillator;
receive medical data from the first defibrillator via the server-client communications connection, and
display a representation of the medical data received via the server-client communications connection,
wherein at least one of the memory of the first defibrillator and the memory of the second defibrillator is configured to store code for a software application that is platform independent.

2. The medical device communications system of claim 1, wherein each of the memory of the first defibrillator and the memory of the second defibrillator is configured to store the code for the software application to establish the server-client communications connection between the first defibrillator and the second defibrillator.

3. The medical device communications system of claim 1, wherein the server-client communications connection is a first server-client communications connection, wherein the memory of the first defibrillator is configured to store the code for the software application to establish a second server-client communications connection between the first defibrillator and an external user device.

4. The medical device communications system of claim 3, wherein the external user device is associated with a user device type of a plurality of user device types, and
wherein the software application is capable of being executed by each user device type of the plurality of user device types.

5. The medical device communications system of claim 1, wherein one of the first defibrillator and the second defibrillator is configured to auto-discover the other of the first defibrillator and the second defibrillator via an auto-discovery protocol.

6. The medical device communications system of claim 5, wherein the server-client communications connection is a first server-client communications connection, and wherein the first defibrillator is further configured to automatically establish a second server-client communications connection with an external device.

7. The medical device communications system of claim 1, wherein the software application permits the data exchange between the first defibrillator and the second defibrillator via the server-client communications connection.

8. The medical device communications system of claim 1, wherein one of the first defibrillator and the second defibrillator is configured to prompt automatic reboot of the other of the first defibrillator and the second defibrillator.

9. The medical device communications system of claim 1, wherein one of the first defibrillator and the second defibrillator is configured to prompt automatic display on the other of the first defibrillator and the second defibrillator a prompt asking for confirmation of implementation of the software application.

10. The medical device communications system of claim 1, wherein one of the first defibrillator and the second defibrillator is configured to take control of the other of the first defibrillator and the second defibrillator.

11. A medical device communications system, comprising:
a communication network;
a first defibrillator comprising at least one first processor and memory, the first defibrillator configured to be enabled as a web server in a server-client communications connection; and
a second defibrillator comprising at least one second processor and memory, the second defibrillator configured to be enabled as a web client in the server-client communications connection and further configured to:
establish the server-client communications connection with the web server of the first defibrillator via the communication network to permit data exchange between the first defibrillator and the second defibrillator;
receive medical data from the first defibrillator via the server-client communications connection, and
display a representation of the medical data received via the server-client communications connection,
wherein each of the memory of the first defibrillator and the memory of the second defibrillator is configured to store code for a software application to establish the server-client communications connection between the first defibrillator and the second defibrillator.

12. The medical device communications system of claim 11, wherein the server-client communications connection is a first server-client communications connection, wherein the memory of the first defibrillator is configured to store code for a software application to establish a second server-client communications connection between the first defibrillator and an external user device.

13. The medical device communications system of claim 12,
wherein the external user device is associated with a user device type of a plurality of user device types, and
wherein the software application is capable of being executed by each user device type of the plurality of user device types.

14. The medical device communications system of claim 11, wherein one of the first defibrillator and the second defibrillator is configured to auto-discover the other of the first defibrillator and the second defibrillator via an auto-discovery protocol.

15. The medical device communications system of claim 14, wherein the server-client communications connection is a first server-client communications connection, and wherein the first defibrillator is further configured to automatically establish a second server-client communications connection with an external device.

16. The medical device communications system of claim 11,
wherein at least one of the memory of the first defibrillator and the memory of the second defibrillator is configured to store code for a software application, and
wherein the software application permits the data exchange between the first defibrillator and the second defibrillator via the server-client communications connection.

17. The medical device communications system of claim 11, wherein one of the first defibrillator and the second defibrillator is configured to prompt automatic reboot of the other of the first defibrillator and the second defibrillator.

18. The medical device communications system of claim 11, wherein one of the first defibrillator and the second defibrillator is configured to prompt automatic display on the other of the first defibrillator and the second defibrillator a prompt asking for confirmation of implementation of the software application on the other of the first defibrillator and the second defibrillator.

19. The medical device communications system of claim 11, wherein one of the first defibrillator and the second defibrillator is configured to take control of the other of the first defibrillator and the second defibrillator.

* * * * *